United States Patent [19]

Cooney et al.

[11] 4,332,899

[45] Jun. 1, 1982

[54] PROCESS FOR PRODUCING MALTASE

[75] Inventors: Charles L. Cooney, Brookline; Eugene J. Schaefer, Somerville, both of Mass.

[73] Assignee: Massachusetts Institute of Technology, Cambridge, Mass.

[21] Appl. No.: 177,709

[22] Filed: Aug. 13, 1980

[51] Int. Cl.³ .................... C12N 15/00; C12N 9/26
[52] U.S. Cl. .................... 435/172; 435/201; 435/255; 435/940
[58] Field of Search ............ 435/201, 255, 256, 172, 435/940

[56] References Cited

U.S. PATENT DOCUMENTS 4,071,407  1/1978  Hall .................... 435/201 X
4,081,326  3/1978  Hall .................... 435/201 X

OTHER PUBLICATIONS

Halvorson et al., in Biochimica et Biophysica Acta, vol. 30, pp. 28-40 (1958).
Halvorson et al. in Biochimica et Biophysica Acta, vol. 67, pp. 42-53 (1963).

*Primary Examiner*—Lionel M. Shapiro
*Attorney, Agent, or Firm*—Arthur A. Smith, Jr.; Paul J. Cook

[57] ABSTRACT

Maltase is produced by growing a mutant of the yeast strain *Saccharomyces italicus* capable of growing in a growth medium utilizing sucrose as the carbon source. Mutants of *Saccharomyces italicus* capable of utilizing sucrose as a carbon source also are provided.

7 Claims, No Drawings

PROCESS FOR PRODUCING MALTASE

BACKGROUND OF THE INVENTION

This invention relates to a new yeast strain and to a process for producing maltase therewith utilizing, as a carbon source, sucrose.

Maltase ($\alpha$-glucosidase, EC 3.2.1.20) is an enzyme presently used in clinical assays for amylase. The maltase is utilized in an intermediate reaction wherein maltose, formed by the action of amylase on an oligosaccharide, is converted to glucose. The glucose is subsequently measured to determine the amylase activity. Presently, maltase is produced from yeast strains such as *Saccharomyces cerevisae* or *Saccharomyces italicus*. The maltase produced from *Saccharomyces italicus* is particularly useful in the assay for amylase in that it will not degrade higher oligosaccharides. Unfortunately, the carbon source is the growth medium for *Saccharomyces italicus* is maltose which is very expensive as compared to possible alternative carbon sources. Attempts to substitute relatively inexpensive sucrose or glucose as the carbon source have proven ineffective with *Saccharomyces italicus*, since regulatory controls in the yeast cells block maltase production when utilizing any other carbon source. Also, contaminating amounts of glucose sometimes present in commercial batches of maltose can have a deleterious effect on maltase production. In addition, the use of maltose as a carbon source has presented production difficulties since the activity of the maltase produced peaks just before the maltose in the medium is depleted thereby requiring that the cells be harvested within a relatively narrow time span.

Accordingly, it would be desirable to provide a means for producing maltase useful in clinical assays for amylase from a yeast strain which does not require maltose as the carbon source. Furthermore, it would be desirable to provide such a means which permits the use of inexpensive sucrose as the carbon source. Furthermore, it would be desirable to provide such a means wherein the activity of the maltase produced is not sharply reduced within a short time span so that the timing of cell harvesting is far less critical than in presently available processes.

SUMMARY OF THE INVENTION

In accordance with this invention, a new strain of yeast is provided comprising mutants and *Saccharomyces italicus*, which, unlike the parent strain, will grow and produce maltase in a medium wherein the carbon source need not be maltose and can include sucrose as the carbon source. The maltase enzyme produced by the process of this invention is particularly useful for assay of amylase.

DESCRIPTION OF THE SPECIFIC EMBODIMENTS

The strain of yeast utilized in the present invention is produced by mutation of *Saccharomyces italicus* with a mutagenic agent such as ultraviolet light, nitroso-guanidine, ethyl methanesulfonate or other known agents. The novel microorganisms of this invention are strains *Saccharomyces italicus* which exhibit the following characteristics.

The novel yeast strains of this invention will grow and produce maltase in a growth medium which can contain, as the carbon source, sucrose. Thus, the strains of yeast utilized in the present invention differ from presently available *Saccharomyces italicus* which are not capable of utilizing sucrose as a carbon source. This strain is also unique in that it produces maltase in the absence of the normal inducer: maltose. Alternative carbon sources which can be utilized by the strain of yeast in this invention include maltose, glycerol, acetate, fructose and glucose. The carbon source is present in the growth medium at concentrations between about 5 g/l and about 60 g/l. For example, with sucrose, the growth medium can contain the sucrose at a concentration of between about 5 and about 50 g/l, preferably between about 40 and about 45 g/l. The growth medium may also contain protein hydrolyzate such as Bacto-Peptone, Difco B118 and a yeast extract such as Bacto Yeast Extract, Difco B127.

In addition, the growth medium contains a source of potassium and phosphorus such as monobasic potassium phosphate or the like, a source of ammonia and sulphur, such as ammonium sulfate and a source of magnesium such as magnesium sulfate. A typical growth medium contained the yeast extract, a digest of meat protein, ammonium sulfate, monobasic potassium phosphate, sodium biphosphate, magnesium sulfate and the carbon source. Typically, the ammonium sulfate comprises between about 2 and about 10 g/l, the monobasic potassium phosphate comprises between about 0.5 and about 3 g/l, the magnesium sulfate comprises between about 0.5 and about 3 g/l, the yeast comprises between about 1 and about 10 g/l and the carbon source comprises between about 20 and about 50 g/l.

The pH of the medium generally is maintained between about 4.5 and about 6.0, preferably about 5.5. It is preferred to control the pH at 5.5 during the course of the fermentation by the addition of sodium hydroxide. Sterile air is sparged into the fermentor at a rate sufficient to meet the needs of the yeast and typically between about 0.5 VVM and about 2.0 VVM. The growth medium is maintained at a temperature between about 22° C. and about 32° C., preferably between about 29° C. and about 31° C. An antifoam product, such as P-2000 manufactured by Dow Chemical Company, can be added at a concentration of about 0.2 ml/l to control foaming.

This fermentation may also be operated in a continuous mode. In such a process, the growth medium is pumped into the fermentor at a constant flowrate and culture broth is continually removed in order to maintain a constant volume in the vessel. At steady state, the growth rate of the cells is equal to the dilution rate: the incoming flowrate divided by the total volume. One advantage of continuous culture is that the productivity is generally much higher than in the case of a batch fermentation. Another advantage in this particular case is that the maltase activity remains constant thus eliminating the need to harvest the cells within a narrow time span as in the case for batch culture.

The cells are then harvested and the maltase enzyme is released by conventional techniques, such as rapid centrifugation followed by sonication, permeabilization of french-pressing. The maltase then is purified such as by ion exchange chromatography, gel filtration, fractionation or the like to remove extraneous materials. The purified maltase then can be stored at low temperatures or can be lyophilized and reconstituted when used. Alternatively, the cells can be used without the recovery of maltase by employing cells of *Saccharomyces italicus* which have been permeabilized by treatment with agents such as dimethyl sulfoxide or toluene. Such permeabilized whole cells permit maltose conversion to glucose without recovery of maltase.

The following examples illustrate the present invention and are not intended to limit the same.

EXAMPLE I

This example illustrates the formation of a mutant of *Saccharomyces italicus* useful in the process of this invention. The selection of this mutant is based on the following conditions: the wild type *Saccharomyces italicus*, ATCC 22185, will not grow on sucrose because it lacks invertase, the normal sucrose-splitting enzyme; sucrose may be catabolized using maltase, but sucrose will not induce maltase formation. Thus, only a mutant which constitutively produces maltase will be able to grow on sucrose. Such a mutant could be generated with one of many well-known mutagenic agents such as ultraviolet light, nitroso-guanidine and ethyl methanesulfonate. The following protocol was employed for mutagensis with ethyl methanesulfonate and selection. An agar slant with the composition: yeast extract 10 g/l, peptone 20 g/l, glucose 20 g/l, agar 20 g/l was innoculated with the wild type *Saccharomyces italicus*. After 24 hours growth, the cells were suspended in 3.5 ml of pH 7.0, 1/15 molar phosphate buffer. One-hundred $\mu$l of ethyl methanesulfonate was added and the suspension was shaken at 30° C. After about one hour, 1 ml of this suspension was added to 40 ml of a 5% sodium thiosulfate solution to inactivate the ethyl methanesulfonate. The cells were then harvested by centrifugation, washed twice and resuspended in a medium composed of: 10 g/l yeast extract, 20 g/l peptone, and 20 g/l glucose. After growing for several generations at 30° C., the cells were centrifuged, washed twice and resuspended in sterile distilled water. Aliquots of 0.1 ml were then plated on a medium comprised of: 6.7 g/l Yeast Nitrogen Base (Difco B391), 20 g/l sucrose, and 20 g/l agar. After 24 hours, several colonies were picked for further study. The chosen mutants were then tested in liquid medium of the same composition but without the agar. Cells were harvested after growth, sonicated and the maltase activity was assayed. All of these mutants produced maltase to some extent since the selection procedure only allows constitutive maltase producers to grow, but some synthesized much more enzyme than others. In other words, different mutational events may effect the same end result: all are constitutive producers but some are more efficient than others. The highest producing mutant of those tested was designated *S. italicus* ATCC 20601.

EXAMPLE II

A comparison was done of maltase production by wild type and constitutive mutants of *S. italicus* grown on various carbon sources. Innoculum grown on 6.7 g/l of Yeast Nitrogen Base (Difco) plus 20 g/l of glucose for 18 hours. Shake flasks containing 50 ml of a culture medium comprised of: 8.9 g/l $(NH_4)_2SO_4$, 5.7 g/l $KH_2PO_4$, 1.7 g/l $Na_2HPO_4$, 1.3 g/l $MgSO_4$. 7 $H_2O$, 5 g/l Yeast Extract, and 25 g/l of the carbon source (except in the case of acetate—8.2 g/l of sodium acetate was useful) at pH 5.5 were started with a 10% innoculum and incubated at 30° C. The cells were harvested at mid-log phase growth and the maltase activity was assayed after sonication of the cells.

| Carbon Source | Maltase (units/gram dry cell weight) | |
|---|---|---|
| | Wild Type | Mutant |
| Sucrose | No growth | 1330 |
| Maltose | 870 | 770 |
| Glycerol | 10 | 1130 |
| Acetate | 10 | 770 |
| Fructose | 10 | 375 |
| Glucose | 10 | 320 |

Thus, the best maltase production occurs with the constitutive mutant grown on sucrose as the carbon source.

EXAMPLE III

This constitutive mutant of *S. Italicus* was grown in a 5-liter fermentor at 30° C., pH 5.5 (controlled by NaOH addition), and aerated at a rate of 1 VVM. Two liters of a culture medium comprised of 8.9 g/l $(NH_4)_2SO_4$, 1.65 g/l $KH_2PO_4$, 1.3 g/l $MgSO_4.7H_2O$, 0.2 g/l $CaCl_2$, 5 g/l Yeast Extract, 2.75 g/l Peptone and 50 g/l of sucrose were innoculated with 200 ml of an 18 hour culture grown on 6.7 g/l of Yeast Nitrogen Base and 40 g/l sucrose. After ten hours of growth, the cells were harvested. The cell density was 10.4 g/l and the maltase activity was 1880 units per gram dry cell weight. This yield was more than 3-fold greater than the typical volumetric yield of the present processes.

EXAMPLE IV

Maltase production by the wild type *S. italicus*, ATCC 22185, and the constitutive mutant of *S. italicus* of this invention were compared in continuous culture experiments. The culture medium for the wild type was comprised of: 30 g/l maltose, 8.9 g/l $(NH_4)_2SO_4$, 1.65 g/l $KH_2PO_4$, 1.3 g/l $MgSO_4$, $7H_2O$, 0.1 g/l $CaCl_2$, 0.2 ml/l P-2000 antifoam, 2 $\mu$g/l biotin, 400 $\mu$g/l pantothenate, 2 mg/l inositol, 400 $\mu$g/l pyridoxine, 400 $\mu$g/l thiamine, 2.78 mg/l $FeSO_4$, $7H_2O$, 2.88 mg/l $ZnSO_4.7H_2O$ 1.6 mg/l $CuSO_4$, $5H_2O$, 2.42 mg/l $Na_2MoO_4.2H_2O$, 2.38 mg/l $CaCl_2.6H_2O$, 1.69 $MnSO_4.H_2O$. The culture medium for the constitutive mutant was the same except that 30 g/l sucrose replaced maltose as the carbon source and the medium was supplemented with the following vitamins: 2 $\mu$g/l folic acid, 400 $\mu$g/l niacin and 200 $\mu$g/l riboflavin. All vitamins were filter sterilized separately while the rest of the components were autoclaved. Two liters of this medium were innoculated with 200 ml of an 18 hour culture of the appropriate strain grown on the same medium. The cells were grown at 30° C., pH 5.5 (controlled by NaOH addition), and aerated at 1 VVM. When the culture reached mid-log phase growth, sterile medium of the same composition was continually pumped into the fermentor and a portion of the broth was pumped out to maintain a constant volume. The growth rate of the cells was thus defined by the rate of addition of fresh medium. Several growth rates were studied for each strain and the steady state maltase activities were as follows:

| Strain | Dilution Rate ($Hr^{-1}$) | Maltase (Units/g) | Cell Mass (g/l) |
|---|---|---|---|
| Wild Type | 0.1 | 420 | 11.1 |
| | 0.2 | 510 | 8.8 |
| | 0.3 | 410 | 3.0 |
| | 0.4 | 410 | 2.4 |
| | 0.06 | 1210 | 13.8 |

-continued

| Strain | Dilution Rate (Hr$^{-1}$) | Maltase (Units/g) | Cell Mass (g/l) |
|---|---|---|---|
| | 0.12 | 1370 | 14.3 |
| Mutant | 0.21 | 1370 | 11.9 |
| | 0.30 | 1120 | 2.8 |

In this case, the mutant produced maltase with approximately three times the specific activity of that made by the wild type, independent of growth rate.

I claim:

1. A biologically pure culture of *Saccharomyces italicus* obtained by mutation of *Saccharomyces italicus* and having the property of producing maltase while growing on all carbon sources selected from the group consisting of maltose, glycerol, acetate, fructose, glucose and sucrose.

2. The process for selecting a mutant of the cells of *Saccharomyces italicus* capable of producing maltase while utilizing sucrose as the primary carbon source which comprises exposing *Saccharomyces italicus* to a mutagenic agent under conditions to effect mutation of *Saccharomyces italicus*, dividing said cells into a plurality of samples, exposing the samples to a growth medium comprising sucrose as the carbon source, and selecting the samples capable of maltase production.

3. The process for forming maltase which comprises growing *Saccharomyces italicus* of claim 1 in a growth medium.

4. The biologically pure culture of claim 1 wherein the *Saccharomyces italicus* mutant is *Saccharomyces italicus* ATCC 20601.

5. The process of claim 3 wherein growth medium is continuously added to said *Saccharomyces italicus* in a culture vessel and removing *Saccharomyces italicus* containing maltase from said culture vessel.

6. The process of claim 3 wherein growth medium is continuously added to said *Saccharomyces italicus* ATCC 20601 in a culture vessel and removing *Saccharomyces italicus* ATCC 20601 containing maltase from said culture vessel.

7. The process of any one of claims 3, 5 and 6 wherein sucrose comprises the carbon source in the growth medium.

* * * * *